(12) United States Patent
Singh et al.

(10) Patent No.: US 11,026,935 B2
(45) Date of Patent: Jun. 8, 2021

(54) FREE BASE CRYSTALLINE FORM OF A COMPLEMENT COMPONENT C5A RECEPTOR

(71) Applicant: CHEMOCENTRYX, INC., Mountain View, CA (US)

(72) Inventors: Rajinder Singh, Belmont, CA (US); Kwok Yau, Sunnyvale, CA (US); Yibin Zeng, Foster City, CA (US); Penglie Zhang, Foster City, CA (US); Rebecca M. Lui, Mountain View, CA (US); Antoni Krasinski, Sunnyvale, CA (US)

(73) Assignee: ChemoCentryx, Inc., San Carlos, CA (US)

( * ) Notice: Subject to any disclaimer, the term of this patent is extended or adjusted under 35 U.S.C. 154(b) by 0 days.

(21) Appl. No.: 17/091,019

(22) Filed: Nov. 6, 2020

(65) Prior Publication Data

US 2021/0137907 A1    May 13, 2021

Related U.S. Application Data

(60) Provisional application No. 62/932,652, filed on Nov. 8, 2019.

(51) Int. Cl.
| | | |
|---|---|---|
| *C07D 211/60* | (2006.01) | |
| *A61K 31/451* | (2006.01) | |
| *A61K 31/675* | (2006.01) | |
| *A61K 39/395* | (2006.01) | |

(52) U.S. Cl.
CPC .......... *A61K 31/451* (2013.01); *A61K 31/675* (2013.01); *A61K 39/3955* (2013.01); *C07D 211/60* (2013.01); *C07B 2200/13* (2013.01)

(58) Field of Classification Search
CPC .................................................. C07D 211/60
USPC ...................................................... 424/133.1
See application file for complete search history.

(56) References Cited

U.S. PATENT DOCUMENTS

| | | | |
|---|---|---|---|
| 7,923,564 B2 | 4/2011 | Thygesen et al. | |
| 8,445,515 B2 * | 5/2013 | Fan .......................... | A61P 9/10 514/326 |
| 8,906,938 B2 | 12/2014 | Fan et al. | |
| 9,126,939 B2 | 9/2015 | Fan et al. | |
| 9,573,897 B2 | 2/2017 | Fan et al. | |
| 10,035,768 B2 | 7/2018 | Fan et al. | |
| 10,660,897 B2 | 5/2020 | Fan et al. | |
| 2010/0311753 A1 | 12/2010 | Fan et al. | |
| 2011/0275639 A1 | 11/2011 | Fan et al. | |
| 2015/0141425 A1 | 5/2015 | Fan et al. | |
| 2017/0065604 A1 | 3/2017 | Fan et al. | |
| 2017/0114017 A1 | 4/2017 | Fan et al. | |
| 2018/0072668 A1 | 3/2018 | Fan et al. | |
| 2019/0062275 A1 | 2/2019 | Fan et al. | |

FOREIGN PATENT DOCUMENTS

| | | |
|---|---|---|
| WO | 2010075257 A1 | 1/2010 |
| WO | 2016/053890 A1 | 4/2016 |

OTHER PUBLICATIONS

International Search Report and Written Opinion dated Feb. 3, 2021 correpsonding to PCT/US2020/059280 filed Nov. 6, 2020; 9 pages.
International Search Report and Written Opinion dated Feb. 8, 2021 corresponding to PCT/US2020/059287 filed Nov. 6, 2020; 9 pages.
Pubchem, SID 237279170, Available Date: Feb. 13, 2015 [retrieved on Jan. 5, 2021]; Retrived form the Internet <URL: https://pubchem.ncbi.nlm.nih.gov/substance /237279170>; 8 pages.
U.S. Appl. No. 17/091,001, filed Nov. 6, 2020, Yau et al.
U.S. Appl. No. 17/091,044, filed Nov. 6, 2020, Singh et al.

* cited by examiner

*Primary Examiner* — Nizal S Chandrakumar
(74) *Attorney, Agent, or Firm* — Mintz Levin Cohn Ferris Glovsky and Popeo PC (57) ABSTRACT

Provided herein is a free base crystalline form of a complement component 5a receptor having the formula of Compound 1

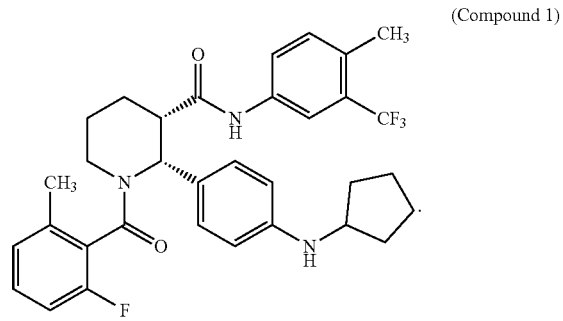

(Compound 1)

Also provided herein are pharmaceutical compositions and methods of treatment using the crystalline free base form of Compound 1 described herein.

9 Claims, 2 Drawing Sheets

FREE BASE CRYSTALLINE FORM OF A COMPLEMENT COMPONENT C5A RECEPTOR

CROSS-REFERENCES TO RELATED APPLICATIONS

This application claims the benefit of priority under 35 U.S.C § 119(e) to U.S. Provisional Application Ser. No. 62/932,652 filed Nov. 8, 2019, the disclosure of which is incorporated herein by reference in its entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The complement system plays a central role in the clearance of immune complexes and in immune responses to infectious agents, foreign antigens, virus infected cells and tumor cells. Inappropriate or excessive activation of the complement system can lead to harmful, and even potentially life-threatening consequences due to severe inflammation and resulting tissue destruction. These consequences are clinically manifested in various disorders including septic shock; myocardial, as well as, intestinal ischemia/reperfusion injury; graft rejection; organ failure; nephritis; pathological inflammation; and autoimmune diseases.

The complement system is composed of a group of proteins that are normally present in the serum in an inactive state. Activation of the complement system encompasses mainly three distinct pathways, i.e., the classical, the alternative, and the lectin pathway (V. M. Holers, *In Clinical Immunology: Principles and Practice*, ed. R. R. Rich, Mosby Press; 1996, 363-391): 1) The classical pathway is a calcium/magnesium-dependent cascade, which is normally activated by the formation of antigen-antibody complexes. It can also be activated in an antibody-independent manner by the binding of C-reactive protein, complexed with ligand, and by many pathogens including gram-negative bacteria. 2) The alternative pathway is a magnesium-dependent cascade which is activated by deposition and activation of C3 on certain susceptible surfaces (e.g. cell wall polysaccharides of yeast and bacteria, and certain biopolymer materials). 3) The lectin pathway involves the initial binding of mannose-binding lectin and the subsequent activation of C2 and C4, which are common to the classical pathway (Matsushita, M. et al., *J. Exp. Med.* 176: 1497-1502 (1992); Suankratay, C. et al., *J. Immunol.* 160: 3006-3013 (1998)).

The activation of the complement pathway generates biologically active fragments of complement proteins, e.g. C3a, C4a and C5a anaphylatoxins and C5b-9 membrane attack complexes (MAC), all which mediate inflammatory responses by affecting leukocyte chemotaxis; activating macrophages, neutrophils, platelets, mast cells and endothelial cells; and increasing vascular permeability, cytolysis and tissue injury.

Complement C5a is one of the most potent proinflammatory mediators of the complement system. (The anaphylactic C5a peptide is 100 times more potent, on a molar basis, in eliciting inflammatory responses than C3a.) C5a is the activated form of C5 (190 kD, molecular weight). C5a is present in human serum at approximately 80 µg/ml (Kohler, P. F. et al., *J. Immunol.* 99: 1211-1216 (1967)). It is composed of two polypeptide chains, α and β, with approximate molecular weights of 115 kD and 75 kD, respectively (Tack, B. F. et al., *Biochemistry* 18: 1490-1497 (1979)). Biosynthesized as a single-chain promolecule, C5 is enzymatically cleaved into a two-chain structure during processing and secretion. After cleavage, the two chains are held together by at least one disulfide bond as well as noncovalent interactions (Ooi, Y. M. et al., *J. Immunol.* 124: 2494-2498(1980)).

Recent work has identified (2R,3S)-2-(4-(cyclopentylamino)phenyl)-1-(2-fluoro-6-methylbenzoyl)-N-(4-methyl-3-(trifluoromethyl)phenyl)piperidine-3-carboxamide, Compound 1 as useful for treating C5a mediated diseases. Despite this identification, the efficient delivery of biologically relevant amounts of Compound 1 remains challenging.

As such, there is a need to identify solid forms of Compound 1 that can improve important biological characteristics such as solubility, dissolution rate, and bioavailability, without sacrificing stability and potency. The present disclosure addresses these needs and provides related advantages as well.

BRIEF SUMMARY OF THE INVENTION

Provided herein is a free base crystalline form of Compound 1, methods of using the same, and pharmaceutical compositions prepared using a free base crystalline form of Compound 1.

In some aspects, provided herein is a free base crystalline form of (2R,3S)-2-(4-(cyclopentylamino)phenyl)-1-(2-fluoro-6-methylbenzoyl)-N-(4-methyl-3-(trifluoromethyl) phenyl)piperidine-3-carboxamide, Compound 1

(Compound 1)

The free base crystalline form of Compound 1 can be characterized using various techniques including, but not limited to, X-ray powder diffraction (XRPD) and differential scanning calorimetry (DSC). Relevant characterizing features from the listed techniques are further described herein.

DETAILED DESCRIPTION OF THE INVENTION

I. General

The present disclosure provides a free base crystalline form of Compound 1. This form is suitable for preparing pharmaceutical compositions including oral solid dosage forms such as tablet, capsule, softgel, oral liquid dosage forms such as solutions and suspensions, topical dosage forms such as semisolids, ointments, pastes, creams and gels, inhalation dosage forms, and parenteral dosage forms such as IV, IM and SC; but not limited to the above-mentioned dosage forms.

II. Definitions

The terms "about" and "around," as used herein to modify a numerical value, indicate a close range around that explicit value. If "X" were the value, "about X" or "around X" would indicate a value from 0.9X to 1.1X, and more preferably, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

"Compound 1" is a chemical compound having an IUPAC name of (2R,3S)-2-(4-(cyclopentylamino)phenyl)-1-(2-fluoro-6-methylbenzoyl)-N-(4-methyl-3-(trifluoromethyl) phenyl)piperidine-3-carboxamide, and the structure shown below:

(Compound 1)

"Substantially free" refers to an amount of 10% or less of another form, preferably 8%, 5%, 4%, 3%, 2%, 1%, 0.5%, or less of another form.

The term "treating" or "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms).

As used herein, a condition is considered "responsive to C5a receptor modulation" if modulation of C5a receptor activity results in the reduction of inappropriate activity of a C5a receptor.

The term "individual" refers to mammals, which includes primates (especially humans), domesticated companion animals (such as dogs, cats, horses, and the like) and livestock (such as cattle, pigs, sheep, and the like), with dosages as described herein. In some embodiments, the term "individual" refers to a human.

III. Detailed Description of Embodiments

A. Free Base Crystalline Form of Compound 1

In some aspects, provided herein is a free base crystalline form Compound 1

(Compound 1)

which is substantially free of other forms of Compound 1.

In some embodiments, the free base crystalline form of Compound 1 is characterized by an X-ray powder diffraction pattern comprising peaks at 8.1, 8.4, 14.1, 16.9, and 19.0 degrees 2θ (±0.2 degrees 2θ). In some embodiments, the free base crystalline form of Compound 1 is further characterized by an X-ray powder diffraction pattern comprising peaks at 12.4, 15.2, 16.1, 24.4, and 24.7 degrees 2θ (±0.2 degrees 2θ). In some embodiments, the free base crystalline form of Compound 1 is characterized by an X-ray powder diffraction pattern substantially in accordance with FIG. 2.

Differential scanning calorimetry (DSC) can also be used to characterize the free base crystalline form of Compound 1. In some embodiments, the free base crystalline form of Compound 1 is characterized by a differential scanning calorimetry thermogram (DSC) comprising an endothermic peak at around 216° C. In some embodiments, the free base crystalline form of Compound 1 is characterized by a melting point onset of about 213° C. as determined by differential scanning calorimetry thermogram (DSC). In some embodiments, the free base crystalline form of Compound 1 is characterized by a differential scanning calorimetry (DSC) thermogram substantially in accordance with FIG. 2.

B. Methods of Making a Free Base Crystalline Form of Compound 1

Compound 1 can be prepared as described previously. See, for example, WO2010/075257, the contents of each are incorporated by reference in their entirety for all purposes.

The free base crystalline form described herein can be prepared as described in the provided Examples. It is understood that there may be more than one crystallization method that will yield the described free base crystalline form.

C. Pharmaceutical Compositions

Provided herein are pharmaceutical compositions comprising a free base crystalline form of Compound 1 or liquid pharmaceutical compositions prepared using the free base crystalline form of Compound 1. Pharmaceutical compositions will include one or more pharmaceutically acceptable excipients.

The pharmaceutical compositions containing the free base crystalline form of Compound 1 may be in a form suitable for oral use, for example, as tablets, troches, lozenges, liquid formulations, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the free base crystalline form of Compound 1 in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and U.S. Pat. No. 4,265,874 to form osmotic therapeutic tablets for control release.

Formulations for oral use may also be presented as hard gelatin capsules wherein the free base crystalline form of Compound 1 is mixed with an inert solid diluent, for example, calcium carbonate, calcium phosphate or kaolin, or as soft gelatin capsules wherein the free base crystalline form of Compound 1 is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions for oral use contain the free base crystalline form of Compound 1 in admixture with excipients suitable for the manufacture of aqueous suspensions. Such excipients are suspending agents, for example sodium carboxymethylcellulose, methylcellulose, hydroxy-propylmethylcellulose, hydroxy-propylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate as well as other poloxamers (e.g. Poloxamer F-68). The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Accordingly, provided herein is aqueous suspension comprising the free base crystalline form of Compound 1 and at least one excipient. In some embodiments, the at least one excipient is at least one suspending agent and/or at least one wetting agent as described above.

Oily suspensions for oral use may be formulated by suspending the free base crystalline form of Compound 1 in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

The pharmaceutical compositions may be in the form of a sterile injectable or infusable aqueous or oleagenous solution or suspension. This solution or suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution, isotonic sodium chloride solution, isotonic aqueous buffer solutions, as well as mixtures of saline, a disintegrating agent such as PEG (e.g. PEG 200, PEG 400, PEG 800, etc), and nonionic surfactants such as Tween80. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables and infusables. Compositions for injectable or infusable administration optionally include a local anesthetic such as lignocaine to ease pain at the site of the injection. Ingredients can be supplied pre-mixed or supplied separately, with mixing of the ingredients occurring shortly before use. In some embodiments, mixing shortly before use is desirable to take advantage of the high initial solubility of the free base crystalline form of Compound 1 in certain liquid formulation mixtures.

Injectable or infusible compositions includes, but is not limited to, intravenous administration, intramuscular administration as well as subcutaneous or intrasternal injection. Accordingly, in some embodiments, provided herein is an injectable or infusible solution comprising Compound 1 and at least one wetting agent or solvent, wherein the intravenous pharmaceutical composition is prepared using the free base crystalline form of Compound 1 described herein. In some embodiments, the injectable or infusible solution is prepared for intravenous administration. In some embodiments, the injectable or infusible solution is prepared for intramuscular administration. In some embodiments, the injectable or infusible solution is prepared for subcutaneous injection. In some embodiments, the injectable or infusible solution is prepared for intrasternal injection. In some embodiments, the at least one wetting agent or solvent in the injectable or infusible pharmaceutical composition includes saline, a disintegrating agent, and nonionic surfactant.

Injectable or infusible compositions can be prepared at any time that is convenient for the medical practitioner or user; this includes shortly before use or well in advance of use. In some embodiments, the composition is prepared shortly before use. Shortly before use includes 0-24 hours before use, 0-10 hours before use, 0-5 hours before use, or 0-1 hours before use. In some embodiments, the injectable or infusible composition is prepared 0-5 hours before use. Well in advance typically refers to one or more days before use. Accordingly, also provided herein are methods of preparing injectable or infusible solution. The method including, dissolving the free base crystalline form of Compound 1 with the at least one wetting agent or solvent to prepare an injectable or infusible solution; and administering the injectable or infusible solution to a subject in need thereof.

Dispersible powders and granules suitable for preparation of an aqueous oral formulations or oral suspensions by the addition of water provide the free base crystalline form of Compound 1 in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The compounds of the present invention may also be administered in the form of suppositories for rectal administration of the drug. These compositions can be prepared by mixing the free base crystalline form of Compound 1 with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of this invention may also be coupled a carrier that is a suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the invention, the compound of the invention is coupled to a polymer or semipermeable polymer matrix that is formed as a stent or stent-graft device.

D. Methods of Treatment

Also provided herein are methods of treating individuals suffering from conditions that are responsive to C5a receptor modulation.

In some aspects provided herein are methods of treating an individual suffering from or susceptible to a disease or disorder involving pathologic activation of C5a receptors, comprising administering to the individual an effective amount of a free base crystalline form of Compound 1 or a pharmaceutical formulation including Compound 1 as described herein.

In some embodiments, the free base crystalline form of Compound 1 described herein is used for treating patients suffering from conditions that are responsive to C5a receptor modulation.

Conditions that can be Treated by C5a Modulation:

Autoimmune disorders—e.g., Rheumatoid arthritis, systemic lupus erythematosus, Guillain-Barre syndrome, pancreatitis, C3 glomerulopathy (C3G), hidradenitis suppurativa (HS), lupus nephritis, lupus glomerulonephritis, immunoglobulin A (IgA) nephropathy, psoriasis, Crohn's disease, vasculitis, irritable bowel syndrome, dermatomyositis, multiple sclerosis, bronchial asthma, pemphigus, pemphigoid, scleroderma, myasthenia gravis, autoimmune hemolytic and thrombocytopenic states, Goodpasture's syndrome (and associated glomerulonephritis and pulmonary hemorrhage), immunovasculitis, tissue graft rejection, hyperacute rejection of transplanted organs; and the like.

Inflammatory disorders and related conditions—e.g., Neutropenia, sepsis, septic shock, Alzheimer's disease, multiple sclerosis, stroke, inflammatory bowel disease (IBD), age-related macular degeneration (AMD, both wet and dry forms), inflammation associated with severe burns, lung injury, and ischemia-reperfusion injury, osteoarthritis, as well as acute (adult) respiratory distress syndrome (ARDS), chronic pulmonary obstructive disorder (COPD), systemic inflammatory response syndrome (SIRS), atopic dermatitis, psoriasis, chronic urticaria and multiple organ dysfunction syndrome (MODS). Also included are pathologic sequelae associated with insulin-dependent diabetes mellitus (including diabetic retinopathy), lupus nephropathy, Heyman nephritis, membranous nephritis and other forms of glomerulonephritis, contact sensitivity responses, and inflammation resulting from contact of blood with artificial surfaces that can cause complement activation, as occurs, for example, during extracorporeal circulation of blood (e.g., during hemodialysis or via a heart-lung machine, for example, in association with vascular surgery such as coronary artery bypass grafting or heart valve replacement), or in association with contact with other artificial vessel or container surfaces (e.g., ventricular assist devices, artificial heart machines, transfusion tubing, blood storage bags, plasmapheresis, plateletpheresis, and the like). Also included are diseases related to ischemia/reperfusion injury, such as those resulting from transplants, including solid organ transplant, and syndromes such as ischemic reperfusion injury, ischemic colitis and cardiac ischemia. The free base crystalline form of Compound 1 described herein may also be useful in the treatment of age-related macular degeneration (Hageman et al, P.N.A.S. 102: 7227-7232, 2005).

Cardiovascular and Cerebrovascular Disorders—e.g., myocardial infarction, coronary thrombosis, vascular occlusion, post-surgical vascular reocclusion, atherosclerosis, traumatic central nervous system injury, and ischemic heart disease. In one embodiment, an effective amount of a free base crystalline form of Compound 1 described herein may be administered to a patient at risk for myocardial infarction or thrombosis (i.e., a patient who has one or more recognized risk factor for myocardial infarction or thrombosis, such as, but not limited to, obesity, smoking, high blood pressure, hypercholesterolemia, previous or genetic history of myocardial infarction or thrombosis) in order reduce the risk of myocardial infarction or thrombosis.

Diseases of Vasculitis—Vasculitic diseases are characterized by inflammation of the vessels. Infiltration of leukocytes leads to destruction of the vessel walls, and the complement pathway is believed to play a major role in initiating leukocyte migration as well as the resultant damage manifested at the site of inflammation (Vasculitis, Second Edition, Edited by Ball and Bridges, Oxford University Press, pp 47-53, 2008). The free base crystalline form of Compound 1 described herein can be used to treat vasculitis, including anti-neutrophil cytoplasmic antibody associate vasculitis (or ANCA-associated vasculitis, which includes microscopic polyangiitis, eosinophilic granulomatosis with polyangitis, and granulomatosis with polyangiitis, which is also known as Wegener's disease), Churg-Strauss syndrome, Henoch-Schonlein purpura, polyateritis nodosa, Rapidly Progressive Glomerulonephritis (RPGN), cryoglobulinaemia, giant cell arteritis (GCA), Behcet's disease and Takayasu's arteritis (TAK).

HIV infection and AIDS—the free base crystalline form of Compound 1 described herein may be used to inhibit HIV infection, delay AIDS progression or decrease the severity of symptoms or HIV infection and AIDS.

Neurodegenerative disorders and related diseases—Within further embodiments, the free base crystalline form of Compound 1 described herein may be used to treat Alzheimer's disease, multiple sclerosis, and cognitive function decline associated with cardiopulmonary bypass surgery and related procedures.

Cancers—The free base crystalline form of Compound 1 described herein are also useful for the treatment of cancers and precancerous conditions in a subject. Specific cancers that can be treated include, but are not limited to, sarcomas, carcinomas, and mixed tumors. Exemplary conditions that may be treated according to the present invention include fibrosarcomas, liposarcomas, chondrosarcomas, osteogenic sarcomas, angiosarcomas, lymphangiosarcomas, synoviomas, mesotheliomas, meningiomas, leukemias, lymphomas, leiomyosarcomas, rhabdomyosarcomas, squamous cell carcinomas, basal cell carcinomas, adenocarcinomas, papillary carcinomas, cystadenocarcinomas, bronchogenic carcinomas, melanomas, renal cell carcinomas, hepatocellular carcinomas, transitional cell carcinomas, choriocarcinomas, seminomas, embryonal carcinomas, wilm's tumors, pleomorphic adenomas, liver cell papillomas, renal tubular adenomas, cystadenomas, papillomas, adenomas, leiomyomas, rhabdomyomas, hemangiomas, lymphangiomas, osteomas, chondromas, lipomas and fibromas.

In some embodiments, the free base crystalline form of Compound 1 described herein can be used for the treatment of diseases selected from the group consisting of sepsis (and associated disorders), COPD, rheumatoid arthritis, lupus nephritis and multiple sclerosis.

In some embodiments, the free base crystalline form of Compound 1 described herein can be used for the treatment of diseases selected from the group consisting of anti-neutrophil cytoplasmic antibody associate (ANCA) vasculitis, C3 glomerulopathy, hidradenitis suppurativa, and lupus nephritis.

Treatment methods provided herein include, in general, administration to a patient an effective amount of a free base crystalline form of Compound 1. Suitable patients include those patients suffering from or susceptible to (i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of the free base crystalline form of Compound 1 described herein. The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). In some embodiments, the free base crystalline form of Compound 1 described herein is administered to a patient (e.g., a human) orally. In some embodiments, the free base crystalline form of Compound 1 described herein is administered to a patient (e.g., a human) intravenously, intramuscularly, or via subcutaneous or intrasternal injection. The effective amount may be an amount sufficient to modulate C5a receptor activity and/or an amount sufficient to reduce or alleviate the symptoms presented by the patient. Preferably, the amount administered is sufficient to yield a plasma concentration of the compound (or its active metabolite, if the compound is a pro-drug) high enough to detectably inhibit white blood cell (e.g., neutrophil) chemotaxis in vitro.

For treatment of most disorders via oral administration, a person of skill in the art may determine the appropriate frequency of administration. In some embodiments, a frequency of administration of 4 times daily or less is preferred. In some embodiments, a dosage regimen of 2 times daily is used. In some embodiments, once daily administration is used. The patient may be administered a free base crystalline form of Compound 1 in a fed or fasted state. In some embodiments, the patient takes the free base crystalline form Compound 1 with food. In some embodiments, the patient takes the free base crystalline form of Compound 1 without food.

For treatment of most disorders via intravenous, intramuscular administration or via subcutaneous or intrasternal injection, a person of skill in the art may determine the appropriate frequency of administration. In some embodiments, the frequency of administration is about once every two weeks. In some embodiments, the frequency of administration is about once every week. In some embodiments, the frequency of administration is about three times a week. In some embodiments, the frequency of administration is about 2 to 5 times a week. In some embodiments, the frequency of administration is about once every other day. In some embodiments, the frequency of administration is about once a day.

It will be understood, however, that the specific dose level and treatment regimen for any particular patient will depend upon a variety of factors including the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

Dosage levels of the order of from about 0.1 mg to about 140 mg per kilogram of body weight per day are useful in the treatment or preventions of conditions involving pathogenic C5a activity (about 0.5 mg to about 7 g per human patient per day). The amount of the free base crystalline form of Compound 1 that may be combined with the carrier materials to produce a single dosage form will vary depending upon the host treated and the particular mode of administration. Dosage unit forms will generally contain between from about 1 mg to about 500 mg of the free base crystalline form of Compound 1. When administered orally, transdermally, intravaneously, or subcutaneously, it is preferred that sufficient amount of the free base crystalline form of Compound 1 be administered to achieve a serum concentration of 5 ng (nanograms)/mL-10 μg (micrograms)/mL serum, more preferably sufficient compound to achieve a serum concentration of 20 ng-1 μg/ml serum should be administered, most preferably sufficient compound to achieve a serum concentration of 50 ng/ml-200 ng/ml serum should be administered. For direct injection into the synovium (for the treatment of arthritis) sufficient amounts of the free base crystalline form of Compound 1 should be administered to achieve a local concentration of approximately 1 micromolar.

E. Combination Therapy

The presently disclosed methods may include combination therapy with one or more additional therapeutic agents that are used in the treatment, prevention, suppression or amelioration of the diseases or conditions involving pathologic activation of C5a receptors. Such one or more additional therapeutic agents may be administered, by a route and in an amount commonly used therefor, contemporaneously or sequentially with the free base crystalline form of Compound 1. When the free base crystalline form of Compound 1 is used contemporaneously with the additional therapeutic agent, a pharmaceutical composition containing such other drugs in addition to the free base crystalline form of Compound 1 is preferred. Accordingly, the pharmaceutical compositions of the present disclosure include those that also contain one or more other active ingredients or therapeutic agents, in addition to the free base crystalline form of Compound 1.

Examples of the one or more additional therapeutic agents are corticosteroids, steroids, immunosuppressants, Immunoglobulin G agonists, Dipeptidyl peptidase IV inhibitors, Lymphocyte function antigen-3 receptor antagonists, Interleukin-2 ligands, Interleukin-1 beta ligand inhibitors, IL-2 receptor alpha subunit inhibitors, HGF gene stimulators, IL-6 antagonists, IL-5 antagonists, Alpha 1 antitrypsin stimulators, Cannabinoid receptor antagonists, Histone deacetylase inhibitors, AKT protein kinase inhibitors, CD20 inhibitors, Abl tyrosine kinase inhibitors, JAK tyrosine kinase inhibitors, TNF alpha ligand inhibitors, Hemoglobin modulators, TNF antagonists, proteasome inhibitors, CD3 modulators, Hsp 70 family inhibitors, Immunoglobulin agonists, CD30 antagonists, tubulin antagonists, Sphingosine-1-phosphate receptor-1 agonists, connective tissue growth factor ligand inhibitors, caspase inhibitors, adrenocorticotrophic hormone ligands, Btk tyrosine kinase inhibitors, Complement C1s subcomponent inhibitors, Erythropoietin receptor agonists, B-lymphocyte stimulator ligand inhibitors, Cyclin-dependent kinase-2 inhibitors, P-selectin glycoprotein ligand-1 stimulators, mTOR inhibitors, Elongation factor 2 inhibitors, Cell adhesion molecule stimulators, Factor XIII agonists, Calcineurin inhibitors, Immunoglobulin G1 agonists, Inosine monophosphate dehydrogenase inhibitors, Complement C1s subcomponent inhibitors, Thymidine kinase modulators, Cytotoxic T-lymphocyte protein-4 modulators, Angiotensin II receptor antagonists, Angiotensin II receptor modulators, TNF superfamily receptor 12A antagonists, CD52 antagonists, Adenosine deaminase inhibitors, T-cell differentiation antigen CD6 inhibitors, FGF-7 ligands, dihydroorotate dehydrogenase inhibitors, Syk tyrosine kinase inhibitors, Interferon type I receptor antagonists, Interferon alpha ligand inhibitors, Macrophage migration inhibitory factor inhibitors, Integrin alpha-V/beta-6 antagonists, Cysteine protease stimulators, p38 MAP kinase inhibitors, TP53 gene inhibitors, Shiga like toxin I inhibitors, Fucosyltransferase 6 stimulators, Interleukin 22 ligands, IRS1 gene inhibitors, Protein kinase C stimulators, Protein kinase C alpha inhibitors, CD74 antagonists, Immunoglobulin gamma Fc receptor IIB antagonists, T-cell antigen CD7 inhibitors, CD95 antagonists, N acetylmannosamine kinase stimulators, Cardiotrophin-1 ligands, Leukocyte elastase inhibitors, CD40 ligand receptor antagonists, CD40 ligand modulators, IL-17 antagonists, TLR-2 antagonists, Mannan-binding lectin serine protease-2 (MASP-2) inhibitors, Factor B inhibitors, Factor D inhibitors, C3aR modulators, C5aR2 modulators, T cell receptor antagonists, PD-1 inhibitors, PD-L1 inhibitors, TIGIT inhibitors, TIM-3 inhibitors, LAG-3 inhibitors, VISTA inhibitors, STING agonists, IDO inhibitors, adenosine receptor modulators, CD39 inhibitors, CD73 inhibitors, antagonists of the chemokine receptors, especially CXCR1, CXCR2, CXCR3, CXCR4, CXCR7, CCR1, CCR2, CCR3, CCR4, CCR5, CCR7, CCR7, CCR9, CX3CR1 and CXCR6, and combinations thereof.

In some embodiments, the additional therapeutic agent used in the therapeutic methods herein, is selected from the group consisting of obinutuzumab, rituximab, ocrelizumab, tositumomab, obinutuzumab, ibritumomab, cyclophosphamide, prednisone, hydrocortisone, hydrocortisone acetate, cortisone acetate, tixocortol pivalate, prednisolone, methylprednisolone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, halometasone, alclometasone dipropionate, beclomethasone, betamethasone valerate, betamethasone dipropionate, prednicarbate, clobetasone-17- butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide and prednicarbate, GB-0998, immuglo, begelomab, alefacept, aldesleukin, gevokizumab, daclizumab, basiliximab, inolimomab, beperminogene perplasmid, sirukumab, tocilizumab, clazakizumab, mepolizumab, fingolimod, panobinostat, triciribine, nilotinib, imatinib, tofacitinib, momelotinib, peficitinib, itacitinib, infliximab, PEG-bHb-CO, etanercept, ixazomib, bortezomib, muromonab, otelixizumab, gusperimus, brentuximab vedotin, Ponesimod, KRP-203, FG-3019, emricasan, corticotropin, ibrutinib, cinryze, conestat, methoxy polyethylene glycol-epoetin beta, belimumab, blisibimod, atacicept, seliciclib, neihulizumab, everolimus, sirolimus, denileukin diftitox, LMB-2, natalizumab, catridecacog, ciclosporin, tacrolimus, voclosporin, voclosporin, canakinumab, mycophenolate, mizoribine, CE-1145, TK-DLI, abatacept, belatacept, olmesartan medoxomil, sparsentan, TXA-127, BIIB-023, alemtuzumab, pentostatin, itolizumab, palifermin, leflunomide, PRO-140, cenicriviroc, fostamatinib, anifrolumab, sifalimumab, BAX-069, BG-00011, losmapimod, QPI-1002, ShigamAbs, TZ-101, F-652, reparixin, ladarixin, PTX-9908, aganirsen, APH-703, sotrastaurin, sotrastaurin, milatuzumab, SM-101, T-Guard, APG-101, DEX-M74, cardiotrophin-1, tiprelestat, ASKP-1240, BMS-986004, HPH-116, KD-025, OPN-305, TOL-101, defibrotide, pomalidomide, Thymoglobulin, laquinimod, remestemcel-L, Equine antithymocyte immunoglobulin, Stempeucel, LIV-Gamma, Octagam 10%, t2c-001, 99mTc-sestamibi, Clairyg, Prosorba, pomalidomide, laquinimod, teplizumab, FCRx, solnatide, foralumab, ATIR-101, BPX-501, ACP-01, ALLO-ASC-DFU, irbesartan+propagermanium, ApoCell, cannabidiol, RGI-2001, saratin, anti-CD3 bivalent antibody-diphtheria toxin conjugate, NOX-100, LT-1951, OMS721, ALN-CCS, ACH-4471, AMY-101, Acthar gel, and CD4+CD25+ regulatory T-cells, MEDI7814, P32, P59, pembrolizumab, nivolumab, atezolizumab, avelumab, durvalumab, CCX354, CCX721, CCX9588, CCX140, CCX872, CCX598, CCX6239, CCX587, CCX624, CCX282, CCX025, CCX507, CCX430, CCX765, CCX758, CCX771, CCX662, CCX650, and combinations thereof.

IV. Examples

The following examples are provided to help illustrate the described invention and are not intended to limit the scope of what the inventors regard as their invention.

Example 1: Preparing a Crystalline Form of Compound 1

Crude Compound 1 was prepared essentially as described in WO 2016/053890.

Figure 1:
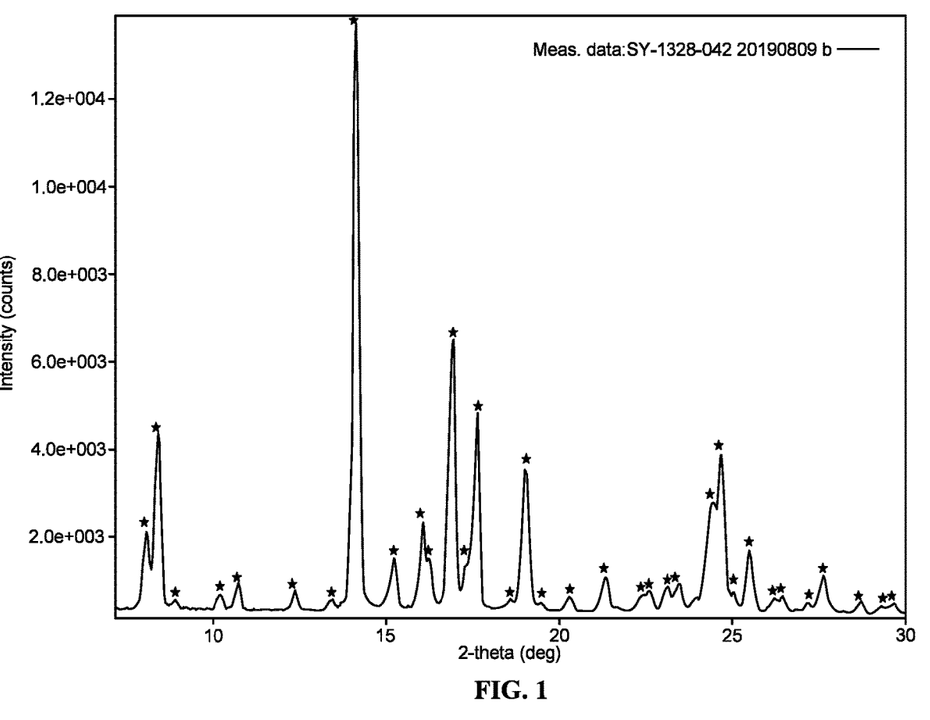
FIG. 1 shows the X-ray powder diffraction (XRPD) pattern of the free base crystalline form described in Example 1.

A crystalline form of Compound 1 was prepared by dissolving 18 g of crude Compound 1 in 50 mL acetone with heating at 40° C. (a concentration of about ~0.36 g/mL). The warm solution was passed through a 10 μm polyethylene filter. The solution was then loaded into rotary evaporator at 30° C. bath temperature and 180 rpm rotational speed. The solid collected was dried further in a 45° C. oven for 1 hour. The XRPD data of the crystalline form is shown in FIG. 1, and the table of peaks measured are listed in Table 1, below.

TABLE 1

| Significant Peaks of Free Base Crystalline Form of Compound 1 Significant Peaks 2-theta (deg) |
| --- |
| 8.06 |
| 8.40 |
| 8.88 |
| 10.20 |
| 10.72 |
| 12.35 |
| 13.44 |
| 14.10 |
| 15.21 |
| 16.05 |
| 16.20 |
| 16.92 |
| 17.28 |
| 17.64 |
| 18.58 |
| 19.00 |
| 19.44 |
| 20.28 |
| 21.32 |
| 22.36 |
| 22.60 |
| 23.14 |
| 23.46 |
| 24.42 |
| 24.66 |
| 25.05 |
| 25.48 |
| 26.20 |
| 26.44 |
| 27.18 |
| 27.60 |
| 28.70 |
| 29.28 |
| 29.60 |

Example 2: Differential Scanning Calorimetry (DSC) and Thermal Gravimetic Analysis (TGA) of the Free Base Crystalline Form of Compound 1

Figure 2:
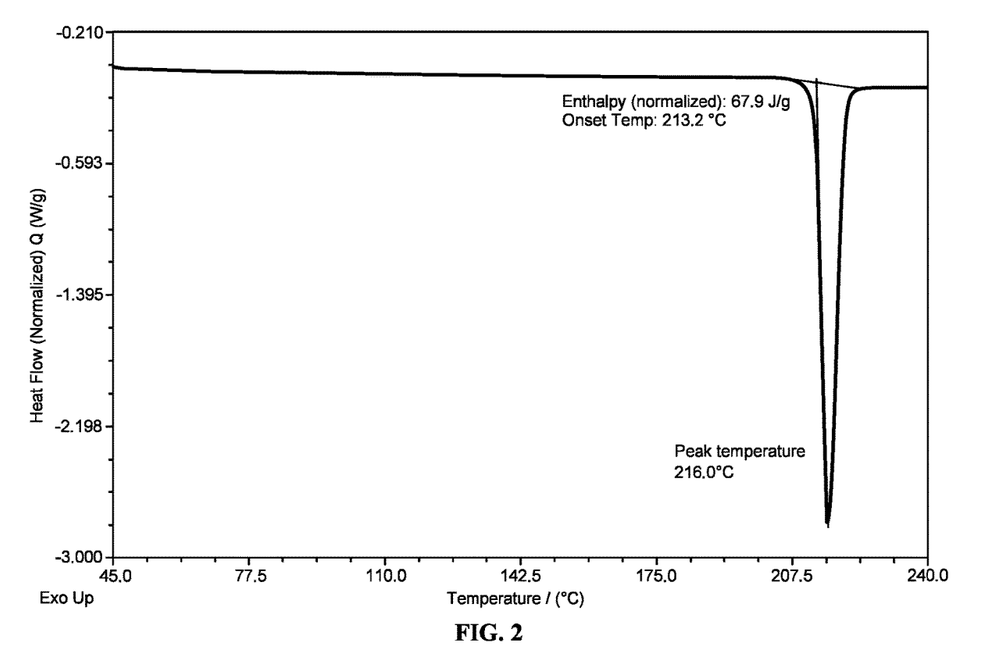
FIG. 2 shows the differential scanning calorimetry (DSC) thermogram of the free base crystalline form of Compound 1.

To evaluate the physical characteristics of the free base crystalline form of Compound 1, differential scanning calorimetry data was collected. Differential scanning calorimeter model DSC25 from TA Instruments ~Waters LLC was used. Sample was weighed into a standard aluminum pan and sealed by a standard aluminum lid with pinhole. The measurement was completed by using 10° C./min scanning rate, under a nitrogen purge. The DSC analysis determined that the free base crystalline form exhibits a melting (on set) of ~213° C. and a endothermic peak at around 216° C. A plot of the DSC thermogram is shown in FIG. 2.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A free base crystalline form of Compound 1

(Compound 1)

characterized by an X-ray powder diffraction (XRPD) pattern comprising peaks at 8.1, 8.4, 14.1, 16.9, and 19.0 degrees 2θ (±0.2 degrees 2θ).

2. The free base crystalline form of claim 1, further characterized by XRPD peaks at 12.4, 15.2, 16.1, 24.4, and 24.7 degrees 2θ (±0.2 degrees 2θ).

3. The free base crystalline form of claim 1, characterized by an X-ray powder diffraction pattern in accordance with FIG. 1.

4. The free base crystalline form of claim 1, further characterized by a differential scanning calorimetry thermogram (DSC) comprising an endothermic peak at around 216° C.

5. The free base crystalline form of claim 1, further characterized by a melting point onset of about 213° C. as determined by differential scanning calorimetry thermogram (DSC).

6. The free base crystalline form of claim 1, further characterized by a DSC in accordance with FIG. 2.

7. A pharmaceutical composition comprising the free base crystalline form of Compound 1 according to claim 1 and at least one pharmaceutically acceptable excipient.

8. An aqueous suspension comprising the free base crystalline form of Compound 1 according to claim 1 and at least one excipient.

9. The aqueous suspension of claim 8, wherein the at least one excipient is at least one suspending agent and/or at least one wetting agent.

* * * * *